(12) United States Patent
Wan

(10) Patent No.: US 8,813,785 B2
(45) Date of Patent: Aug. 26, 2014

(54) FLUID SELECTION VALVE

(71) Applicant: PromoChrom Technologies Ltd., Surrey (CA)

(72) Inventor: Haibin Wan, Richmond Surrey (CA)

(73) Assignee: PromoChrom Technologies Ltd., Surrey (CA)

( * ) Notice: Subject to any disclaimer, the term of this patent is extended or adjusted under 35 U.S.C. 154(b) by 0 days.

(21) Appl. No.: 13/713,996

(22) Filed: Dec. 13, 2012

(65) Prior Publication Data

US 2013/0174927 A1    Jul. 11, 2013

(30) Foreign Application Priority Data

Jan. 9, 2012    (CN) .......................... 2012 1 0004061
Jan. 9, 2012    (CN) .......................... 2012 2 0006082

(51) Int. Cl.
*F16K 11/074*    (2006.01)
*F16K 11/00*    (2006.01)
*F16K 5/22*    (2006.01)

(52) U.S. Cl.
USPC ................. 137/625.46; 137/240; 137/625.15

(58) Field of Classification Search
CPC ... F16K 11/074; F16K 11/0743; G01N 30/20; G01N 2030/202; G01N 35/1097; B01D 2259/40005
USPC ............. 137/625.46, 625.11, 625.13, 625.15, 137/625.47, 240
See application file for complete search history.

(56) References Cited

U.S. PATENT DOCUMENTS

| 5,803,117 | A | * | 9/1998 | Olsen et al. ............... 137/625.15 |
| 6,155,123 | A | * | 12/2000 | Bakalyar .................... 73/864.83 |
| 6,161,583 | A | * | 12/2000 | Morris ..................... 137/625.21 |
| 7,503,203 | B2 | * | 3/2009 | Gamache et al. ............ 73/23.42 |
| 8,382,979 | B2 | * | 2/2013 | Maeda et al. ............... 210/198.2 |
| 8,656,955 | B2 | * | 2/2014 | Price ........................ 137/625.46 |
| 2003/0098076 | A1 | * | 5/2003 | Nichols .................... 137/625.46 |
| 2007/0144594 | A1 | * | 6/2007 | Moon et al. .............. 137/625.46 |
| 2010/0032603 | A1 | * | 2/2010 | Wilen ......................... 251/208 |
| 2010/0058841 | A1 | * | 3/2010 | Wilen .......................... 73/61.56 |
| 2010/0206411 | A1 | * | 8/2010 | Maeda et al. ............ 137/625.17 |

FOREIGN PATENT DOCUMENTS

JP    04-204156    7/1992

* cited by examiner

*Primary Examiner* — Elizabeth Houston
*Assistant Examiner* — Michael R Reid
(74) *Attorney, Agent, or Firm* — Oyen Wiggs Green & Mutala LLP

(57) ABSTRACT

A multiple fluid selection valve including a stator and a rotor is provided. The stator includes a stator interface and a plurality of ports arranged into a plurality of port groups. Each port group has a common port and non-common ports. The non-common ports include a first non-common port and a second non-common port. The rotor includes a plurality of first channels, each first channel extending from an axial center of the rotor to at least a point on the rotor interface alignable with the common ports for fluid communication therewith. The rotor also includes a plurality of second channels, each second channel extending from at least a point on the rotor interface alignable with the common ports for fluid communication therewith to at least a point on the rotor interface alignable with the first non-common ports and/or the second non-common ports for fluid communication therewith.

15 Claims, 10 Drawing Sheets

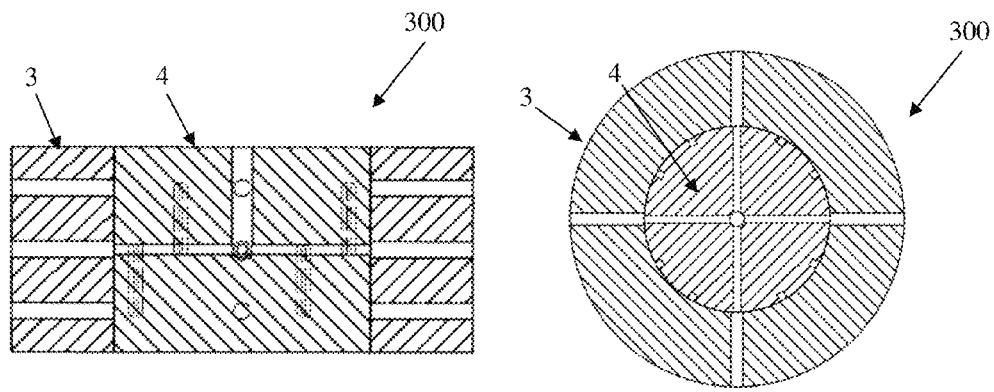
FIG. 12                    FIG. 13
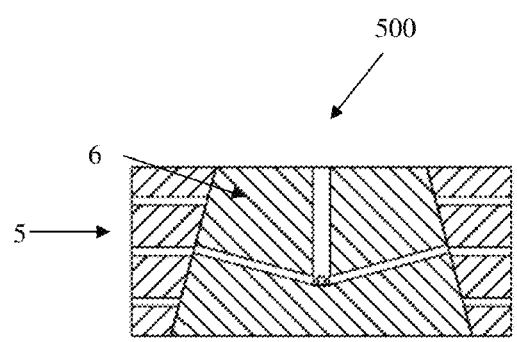
FIG. 14

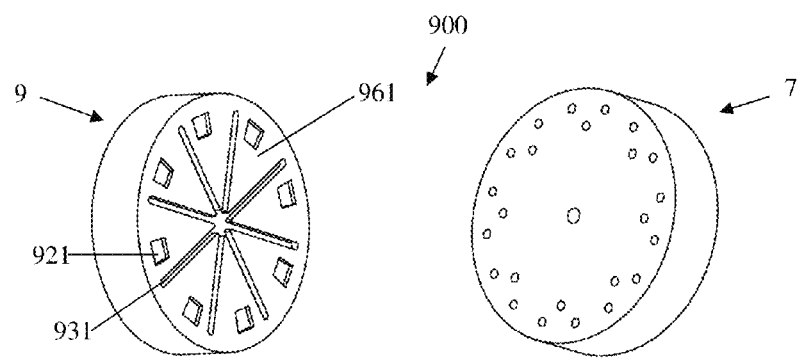
FIG. 20
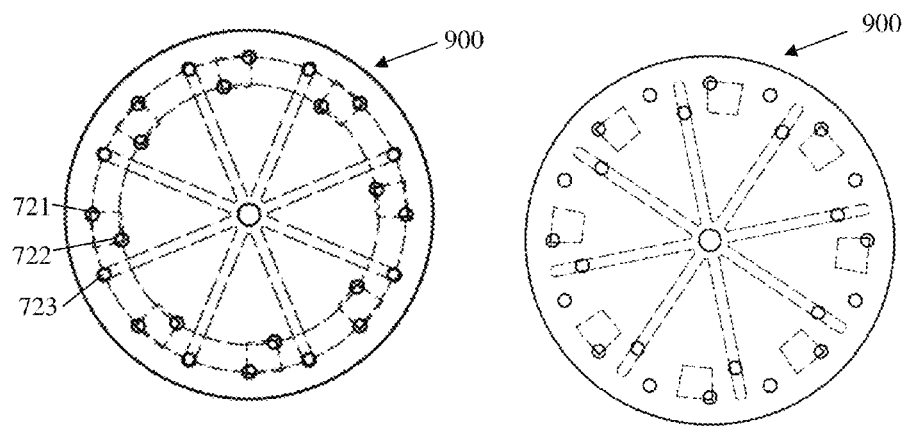
FIG. 21
FIG. 22

FLUID SELECTION VALVE

RELATED APPLICATION

This application claims priority from Chinese Patent Application No. 201210004061.6 filed on 9 Jan. 2012 and Chinese Utility Model Application No. 201220006082.7 filed on 9 Jan. 2012, both of which are hereby incorporated by reference.

TECHNICAL FIELD

The present invention relates to rotary valves, and in particular to rotary fluid selection valves for use with chemical sample handling apparatus.

BACKGROUND

Sample handling apparatus are used for cleanup and enrichment of chemical samples prior to chemical analysis. Typical operating procedures of such apparatus includes eluting a column packed with a sorbent using a solvent to wet the sorbent bed, loading a sample to the column, eluting the column again with a solvent to remove the interfering components from the sample, and then washing down the target component(s) in the sample from the column using a solvent and collecting the target component(s) fraction for further analysis. In conventional sample handling apparatus, valves are switched to divert solvents and sample fluids.

There are two general types of sample handling apparatus: single channel apparatus that process samples sequentially and multi-channel apparatus for parallel processing of multiple samples. Multi-channel apparatus offer faster sample throughput but involves more valves and more complicated tubing connections and control, resulting in higher cost.

Valves commonly used in conventional sample handling apparatus are solenoid driven valves (e.g., solenoid flow selection valves and isolation valve manufactured by Bio-Chem Fluidics, Boonton, N.J., USA) and rotary valves (e.g., multi-position valves manufactured by VICI Co., Houston, Tex., USA). A rotary valve comprises a stator with connection ports and a rotor with channels. Fluid can be diverted to a targeted port by rotating the rotor relative to the stator.

Examples of conventional multi-channel sample handling apparatus may be found in: 1) U.S. Pat No. 5,660,792 (Toshio Koike et al.); 2) AutoTrace SPE instrument brochure by Dionex Corporation (LPN2161, 02/09); 3) Automated liquid handling product guide by Gilson, Inc. (LT303041-11, page 40). Conventional designs such as these require at least one conventional valve for each channel.

Improved and cost-effective apparatus and methods for multi-channel sample handling are desirable.

SUMMARY OF THE INVENTION

The present invention provides a fluid selection valve for parallel preparation of multiple samples. Such a valve is particularly useful for apparatus for automatic sample cleanup and enrichment in chemical analysis, such as a multi-channel automated solid phase extraction instrument.

In one aspect, a fluid selection valve comprising a stator and a rotor is provided. The stator comprises: a stator interface and a plurality of ports. The plurality of ports is arranged into a plurality of port groups. Each port group comprises at least three ports of which one is designated as a common port and the others are designated as non-common ports. The non-common ports comprise a first non-common port and a second non-common port. Each of the common ports, first non-common ports and the second non-common ports are circularly arranged at the stator interface. The rotor comprises a rotor interface abutting said stator interface. The rotor also comprises a plurality of first channels, each first channel extending from an axial center of the rotor to at least a point on the rotor interface alignable with the common ports for fluid communication therewith. The rotor also comprises a plurality of second channels, each second channel extending from at least a point on the rotor interface alignable with the common ports for fluid communication therewith to at least a point on the rotor interface alignable with the first non-common ports and/or the second non-common ports for fluid communication therewith. At least one of the stator and the rotor comprises a central port located in an axial center thereof. The rotor is coaxially rotatable relative to the stator to configure the fluid selection valve in at least three different positions; wherein in a first position, the common ports are in fluid communication with the central port via the first channels; wherein in a second position, the common ports are in fluid communication with the first non-common ports via the second channels; and wherein in a third position, the common ports are in fluid communication with the second non-common ports via the second channels.

An angular measure between a first channel and an adjacent first channel may be equal to an angular measure between a common port in a port group and a common port in an adjacent port group.

In one aspect the central port of the fluid selection valve may located in the axial center of the stator. The first channels and the second channels may extend in a plane generally orthogonal to the axis of the rotor. The rotor and the stator may each comprise a substantially disc-shaped body. The first channels may comprise generally linear grooves on a surface of the rotor interface, or bores within the rotor below a surface of the rotor interface.

The circular arrangements of the common ports, first non-common ports and the second non-common ports at the stator interface may overlap. The second channels may comprise generally linear grooves on a surface of the rotor interface. The plurality of ports may comprise four port groups, and each port group may comprise three ports of which one is designated as the common port and the other two are designated as the non-common ports, and wherein the rotor comprises four first channels and four second channels, wherein the length of each first channel is equal to a distance of the common port to the central port, and wherein the length of each second channel is equal to a distance of the common port to the non-common ports within the same port group.

The common ports may be located on a first imaginary circle, the non-common ports may be located on a second imaginary circle, and the first circle may be concentric but non-overlapping with the second circle. The second channels may comprise a generally trapezoidal shape or a generally cross shape.

In one aspect the central port of the fluid selection valve may be located in the axial center of the rotor. The first channels may extend in a plane generally orthogonal to the axis of the rotor and the second channels extend in a plane generally parallel to the axis of the rotor. The stator may comprise an annular or frustoconical annular body and the rotor may comprise a cylindrical or frustoconical body configured for fitting engagement within the annular or frustoconical annular body of the stator.

BRIEF DESCRIPTION OF DRAWINGS

In drawings which show non-limiting embodiments of the invention:

FIG. 12 is a side sectional view of the fluid selection valve of FIG. 10.

FIG. 13 is a top sectional view of the fluid selection valve of FIG. 10.

FIG. 14 is a side sectional view of a fluid selection valve according to an example embodiment of the present invention.

FIG. 20 is an exploded isometric view of a fluid selection valve according to an example embodiment of the present invention.

FIG. 21 is a top view of the fluid selection valve of FIG. 20 showing a port connection pattern.

FIG. 22 is a top view of the fluid selection valve of FIG. 20 showing another port connection pattern.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

According to aspects of the invention, the fluid selection valve comprises a stator having a plurality of ports for connecting fluid lines thereto, and a rotor coaxially rotatable with respect to the stator. The rotor comprises channels. The ports on the stator are arranged in a plurality of groups. The stator has at least two groups of ports. Each group has at least three ports, among which one of the ports is used as common port. The common port may be used to connect to a syringe or a pump, for example. The other two ports in the group may be used to connect with a sample and a column, for example. The stator may additionally or alternatively comprise a central port. The central port may be used to connect with an elution solvent or another fluid selection valve for multiple elution solvents. The channels on the rotor are arranged such that by rotating the rotor the common port in each group of the ports of the stator can be connected with one of the other two ports in the group or to the port located in the center of the stator. Each group of the ports can be used to construct a channel for a multi-channel sample handling apparatus. By switching the valve once, all the channels are switched. The structure and the control of a multi-channel sample handling apparatus are considerably simplified by using the selection valve of the invention.

Figure 1:
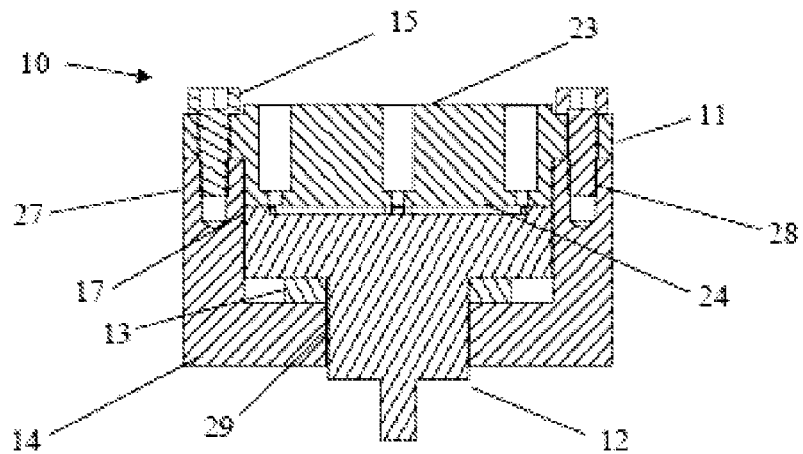
FIG. 1 is a side sectional view of a fluid selection valve according to an example embodiment of the present invention.
Figure 2:
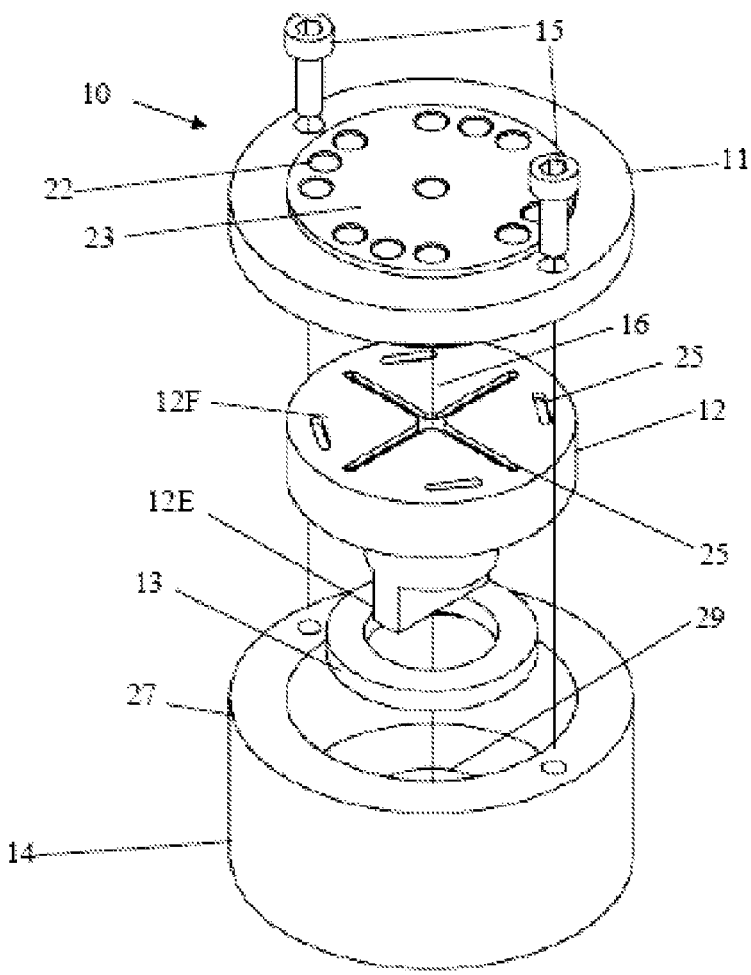
FIG. 2 is an exploded isometric view of the fluid selection valve of FIG. 1.

FIGS. 1 and 2 illustrate a selection valve 10 constructed in accordance with a first example embodiment of the present invention. Valve 10 comprises a stator 11 and a rotor 12. Stator 11 has an upper face 23 and an interface 24. Stator 11 includes a plurality of ports 22 that vertically extend through the body of stator 11. Ports 22 are configured to receive fluid lines. Rotor 12 has an interface 12F and an extension 12E for engaging a drive motor (not shown). Rotor 12 includes a plurality of channels 25 for fluid communication with ports 22, as described in further detail below.

Stator 11 and rotor 12 are received in a housing 14. Stator 11 is rigidly fixed to upper annular sidewalls 27 of housing 14 by a plurality of fasteners 15. Fasteners 15 may for example be screws which are received in corresponding threaded holes 28 in upper annular sidewalls 27. In other embodiments, stator 11 may be fixed to housing 14 in other ways.

Rotor 12 is held within housing 14 by stator 11. Rotor extension 12E extends through an opening 29 at the bottom of housing 14. Rotor 12 is coaxially rotatable relative to stator 11 about axis 16 of stator 11. Some embodiments may include a washer 17 to facilitate a sealed connection and relative rotation between rotor upper face 12F and stator lower face 4. Some embodiments may also include a washer 13 to facilitate a sealed connection and relative rotation between rotor 12 and housing 14.

Figure 3:
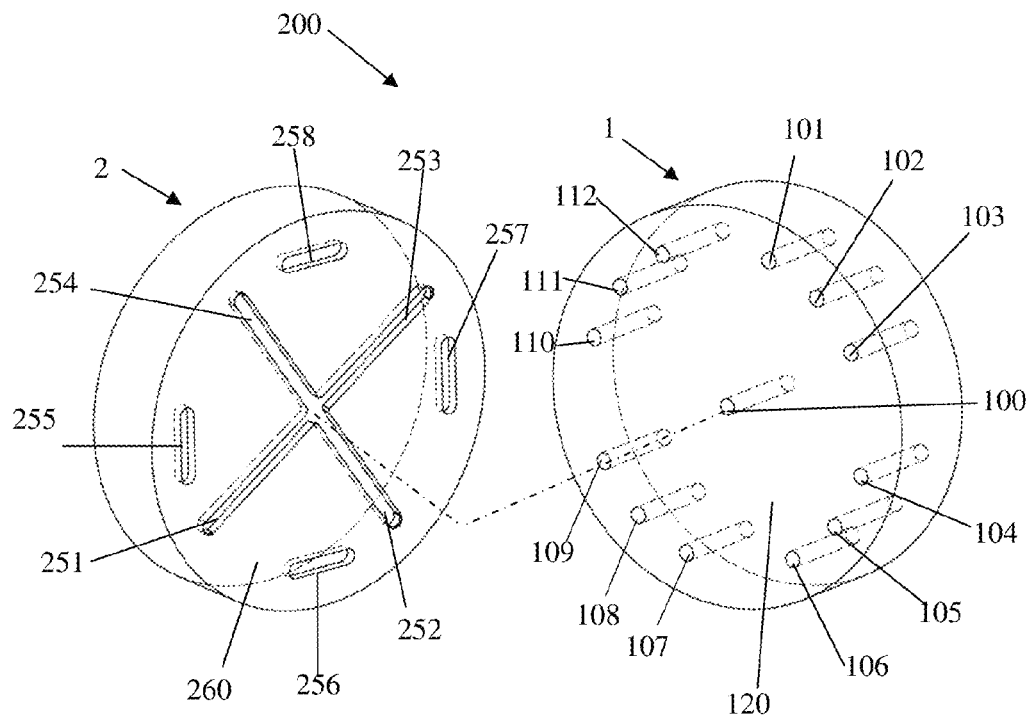
FIG. 3 is an exploded view of the stator and the rotor of a fluid selection valve according to an example embodiment of the present invention.
Figure 4:
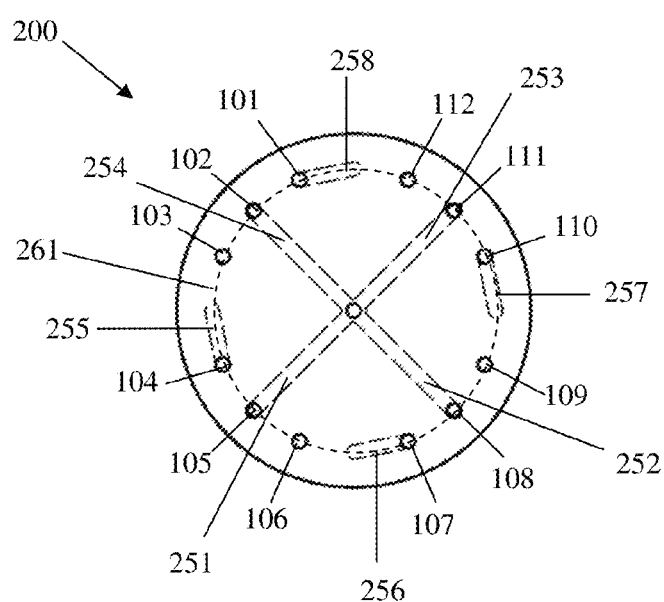
FIG. 4 is a top view of the fluid selection valve of FIG. 3 showing a port connection pattern.
Figure 5:
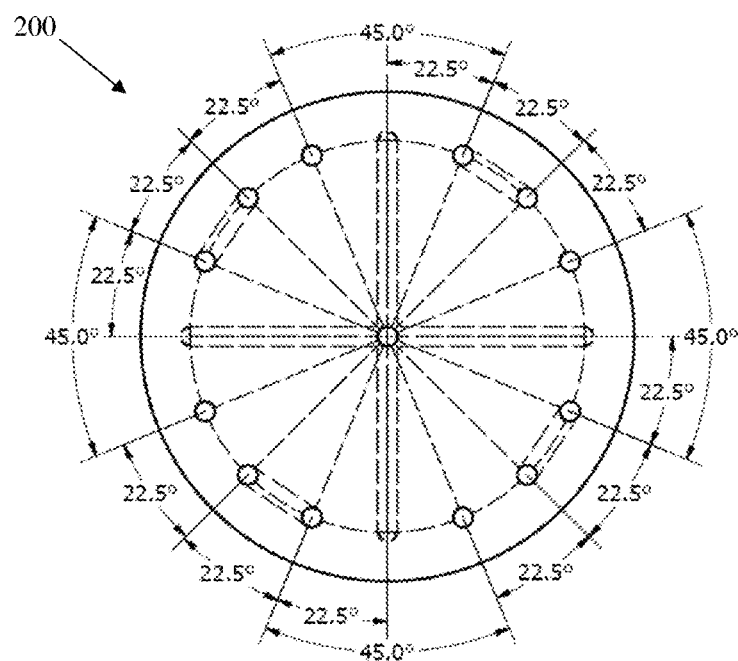
FIG. 5 is a top view of the fluid selection valve of FIG. 3 showing another port connection pattern.

FIGS. 3 to 5 show selection valve 200 according to an example embodiment. Selection valve 200 is similar to selection valve 10 but some elements such as the stator ports have different dimensions. FIGS. 3 to 5 show a simplified view of selection valve 200, e.g. selection valve 200 is shown without its equivalents of housing 14 and rotor extension 12E. Selection valve 200 comprises a stator 1 and a rotor 2, both of which are substantially disc-shaped. Central port 100 extends through a center axis of stator 1. A plurality of additional ports is concentrically arranged around central port 100 along an imaginary circle 261. The illustrated embodiment has twelve additional ports. These twelve ports are divided into four groups, each group consisting of three ports. Ports 101 to 103 define group 1, ports 104 to 106 define group 2, ports 107 to 109 define group 3, and ports 110 to 112 define group 4. Each group has a central or common port, namely ports 102, 105, 108, and 111 respectively. In other embodiments, the stator may have two, three, or more than four groups of ports. In other embodiments, each port group may consist of more than three ports.

Channels on rotor 2 are formed with two types of channels on interface 260 of rotor 2. A plurality of first channels radiates from the axial center of rotor 2 or center of interface 260. In the illustrate embodiment, the first channels are linear grooves 251, 252, 253 and 254. As shown in FIG. 4, grooves 251, 252, 253, and 254 substantially correspond in length and location to radii of imaginary circle 261. The first channels extend from an axial center of the rotor to at least a point alignable with the one or more of the ports to provide fluid communication between central port 100 and the one or more of the surrounding ports (i.e., ports 101-112), or at least between central port 100 and common ports 102, 105, 108, and 111.

An angular measure between a first channel and an adjacent first channel is equal to an angular measure between a common port in a port group and a common port in an adjacent port group. In the illustrated embodiment, the angular measures are both 90 degrees.

A plurality of second channels is arranged in a concentric manner around the center of interface 260 of rotor 2 along a path corresponding to imaginary circle 261 when rotor 2 and stator 1 are fitted together (see FIG. 4). In the illustrated embodiment, the second channels are linear grooves 255, 256, 257, and 258. The second channels extend from a point alignable with the common ports to a point alignable with their adjacent ports in each group to provide fluid communication between the common ports and their adjacent ports. Both first channels and second channels of rotor 2 extend in a plane generally orthogonal to the central axis of rotor 2.

In FIG. 4, the common ports 102, 105, 108, and 111 in the four groups are in fluid communication with central port 100 via grooves 251 to 254 respectively, and other ports are blocked. FIG. 5 is a top view of FIG. 3 after rotor 2 is turned 45 degrees clockwise. As shown in FIG. 5, common ports 102, 105, 108, and 111 in each group are in fluid communication with one of their adjacent port in their group, namely ports 103, 106, 109 and 112, respectively. If rotor 2 turns a further 22.5 degrees clockwise, common ports 102, 105, 108, and 111 in each group will be in fluid communication with the other adjacent port in their group, namely ports 101, 104, 107 and 110, respectively.

Accordingly, by selectively rotating rotor 2 coaxially with respect to stator 1, common ports 102, 105, 108, and 111 in each group can have one of three statuses: 1) fluid communication with a first one of their adjacent ports in the same group; 2) fluid communication with a second one of their adjacent ports in the same group; or 3) fluid communication with central port 100. In the illustrated embodiment, the connection statuses of all four groups are the same at any one time.

Figure 6:
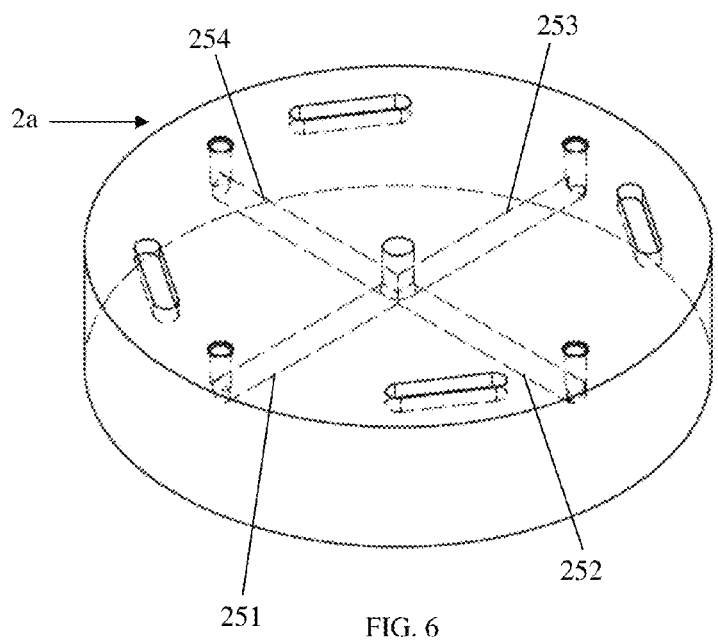
FIG. 6 is an isometric view of a rotor of a fluid selection valve according to an example embodiment of the present invention.

FIG. 6 is an isometric simplified view of a rotor 2a according to another example embodiment. The only difference between rotor 2a and rotor 2 is that first channels 251-254 comprise bores disposed below the surface of the rotor interface in the second embodiment. The design of rotor 2a is useful to reduce cross-contamination of samples on the rear surface of the stator.

Figure 7:
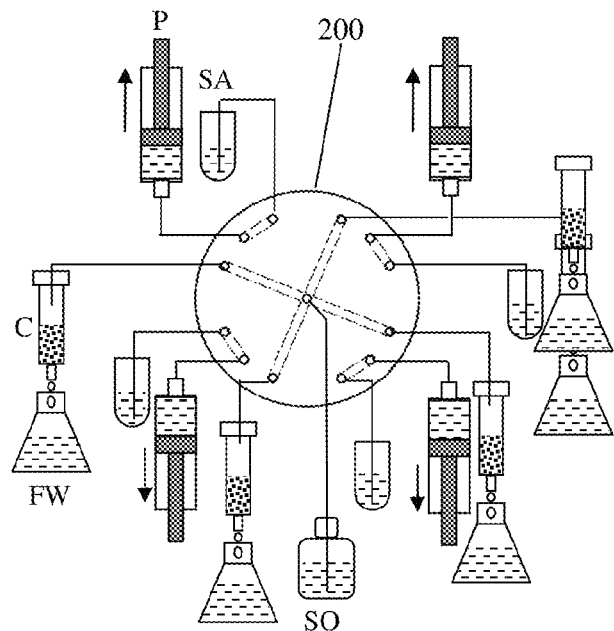
FIG. 7 is a schematic diagram showing an application of the fluid selection valve of FIG. 3 in a 4-channel sample handling apparatus configured in a first connection status according to an example embodiment of the present invention.
Figure 8:
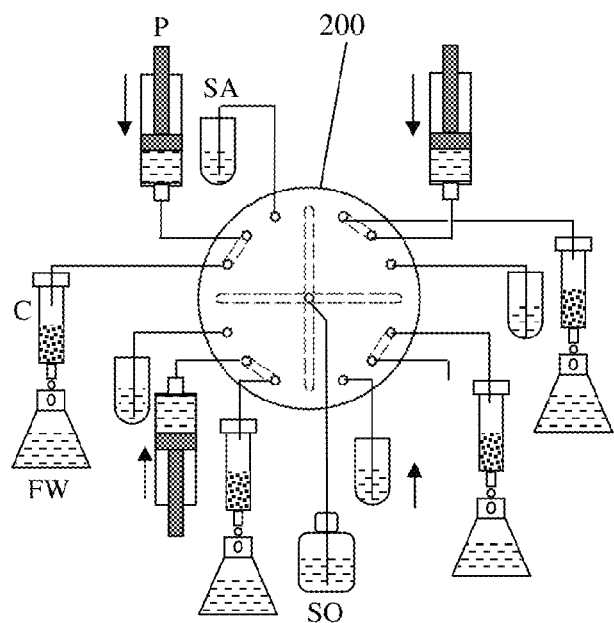
FIG. 8 is a schematic diagram of the application of FIG. 7 with the apparatus configured in a second connection status.
Figure 9:
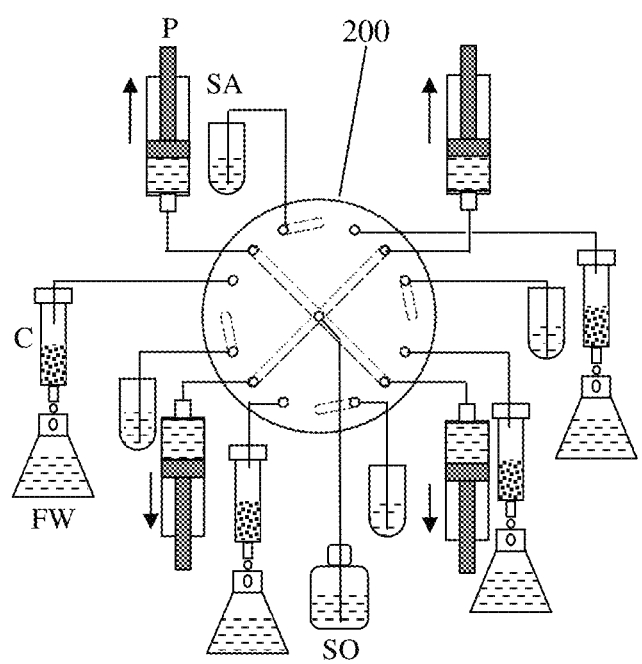
FIG. 9 is a schematic diagram of the application of FIG. 7 with the apparatus configured in a third connection status.

FIGS. 7 to 9 demonstrate an example of a four channel automated solid phase extraction apparatus constructed using selection valve 200 as described above. Each group of the ports can be used to construct a channel for a multi-channel sample handling apparatus. For example, a common port may be in fluid communication with a pump or a syringe P, the other two ports in the group may be in fluid communication with sample SA and solid phase extraction column C respectively. By rotating rotor 2, valve 200 can divert sample SA or elution solvent SO to the columns C. Fraction or water (FW) is collected from column C. Fraction or waste (FW) is collected from column C. In FIG. 7, pumps P are in fluid communication with samples SA through a second channel connecting a common port and a non-common port to draw in samples. In FIG. 8, pumps P are in fluid communication with columns C through a second channel connecting a common port and the other non-common port to deliver the samples to the columns. In FIG. 9, pumps P are in fluid communication with solvent SO through the first channels and the common ports to draw in solvent SO. Solvent SO can then be delivered to columns C by configuring the apparatus as in FIG. 8 again.

When more than one type of solvent are required for the elution, central ports 100 may be in fluid communication with a multi position selection valve (e.g., a multi-position valve manufactured by VICI Co., Houston, Tex., USA). The multi position selection valve can then be in fluid communication with the solvents.

By switching the valve once, all the channels are switched. This simplifies the control procedures. When more channels are needed for a sample handling apparatus, more port groups can be added to the fluid selection valve to accommodate the change. It is not necessary to add extra valves. With the increase of the channels in an apparatus, the advantages of the present invention become more significant over conventional apparatus that need at least one valve for each channel.

Figure 10:
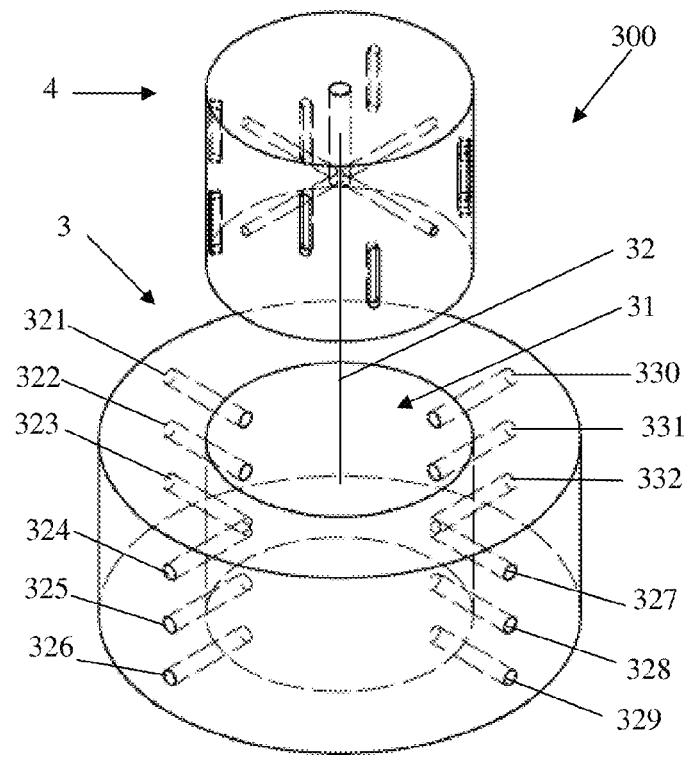
FIG. 10 is an exploded isometric view of a fluid selection valve according to an example embodiment of the present invention.

FIGS. 10 to 13 illustrate selection valve 300 according to an example embodiment. In FIG. 10, rotor 4 is offset from its normal operating position for purpose of illustration. Rotor 4 has a generally cylindrical shape and stator 3 has a generally annular shape. Stator 3 includes ports 321, 322, 323 which form group 1 with port 322 as the common port; ports 324, 325, 326 which form group 2 with port 325 as the common port; ports 327, 328, 329 which form group 3 with port 328 as the common port; and ports 330, 331, 332 which form group 4 with port 331 as the common port.

Figure 11:
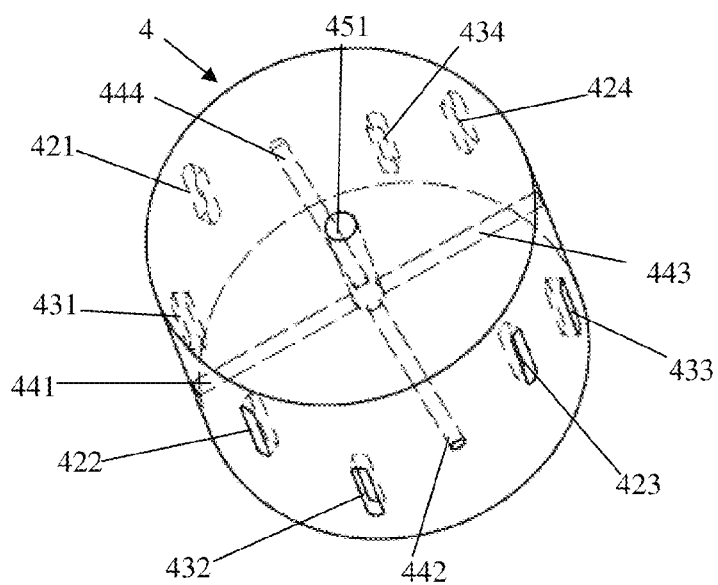
FIG. 11 is an isometric view of the rotor of the fluid selection valve of FIG. 10.

FIG. 11 is a simplified view of a rotor 4 of selection valve 300. Second channels include grooves 421 to 424 and 431 to 434. Grooves 421 to 424 are used to provide fluid communication between the common ports and their adjacent non-common ports above them. Grooves 431 to 434 are used to provide fluid communication between the common ports and their adjacent non-common ports below them. First channels 441 to 444 originate from the center of rotor 4 and are used to provide fluid communication between the common ports and central port 451 at axial center of rotor 4. Rotor 4 is received in chamber 31 of stator 3 as shown in FIGS. 12 and 13 and is rotatable about axis 32. Each common port in the four groups of ports can achieve the same connection statuses as shown in FIGS. 7 to 9.

Figure 15:
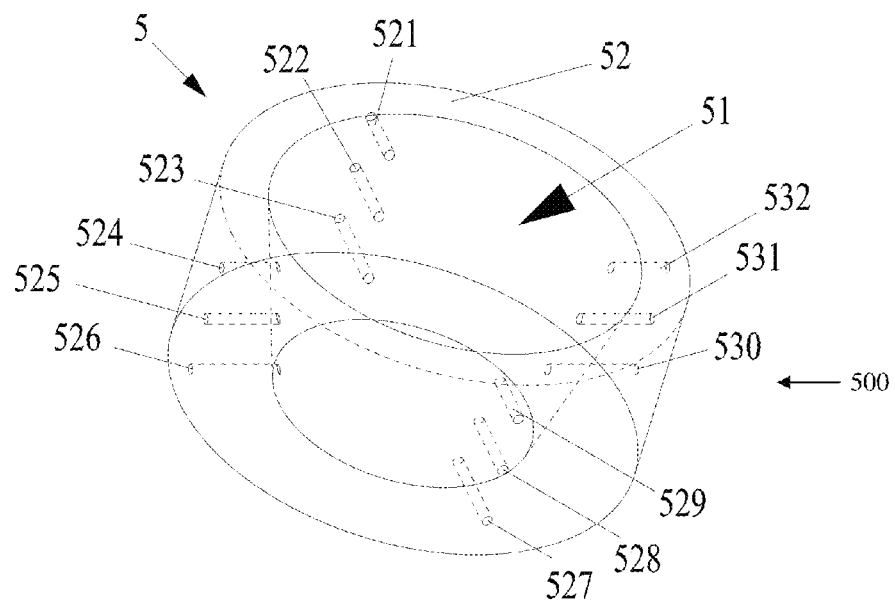
FIG. 15 is an isometric view of the stator of the fluid selection valve of FIG. 14.
Figure 16:
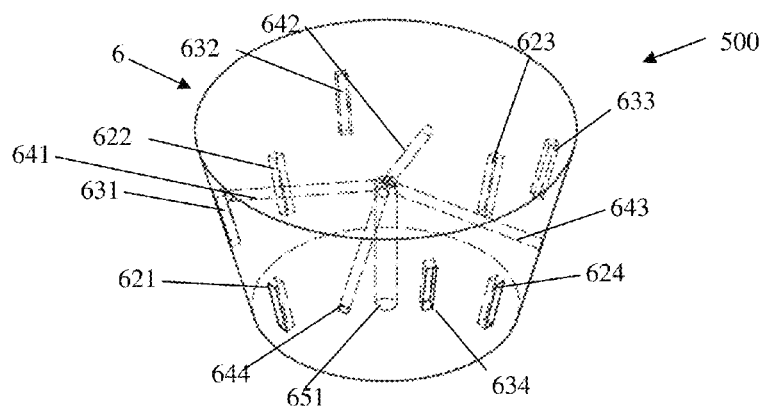
FIG. 16 is an isometric view of the rotor of the fluid selection valve of FIG. 14.

FIGS. 14 to 16 illustrate selection valve 500 according to an example embodiment. Selection valve 500 includes rotor 6 and stator 5. Rotor 6 has a generally frustoconical shape. Stator 5 is of a generally frustoconical annular shape. Stator 5 has a chamber 51 which receives rotor 6. Stator 5 includes ports 521, 522, 523 which form group 1 with port 522 as the common port; ports 524, 525, 526 which form group 2 with port 525 as the common port; ports 527, 528, 529 which form group 3 with port 528 as the common port; and ports 530, 531, 532 which form group 4 with port 531 as the common port.

FIG. 16 is a view of rotor 6 of selection valve 500. First channels include grooves 621 to 624 and 631 to 634. Grooves 621 to 624 are used to provide fluid communication between the common ports and their adjacent non-common ports below them. Grooves 631 to 634 are used to provide fluid communication between the common ports with their adjacent non-common ports above then. Channels 641 to 644 radiating from the center of the rotor are used to provide fluid communication between the common ports and a central port 651 at axial center of rotor 6. Rotor 6 is received in chamber 51 of the stator 5 as shown in FIG. 14. By selectively rotating rotor 6, each common port in the four groups of the ports can achieve the same connection statuses as shown in FIGS. 7 to 9.

Figure 17:
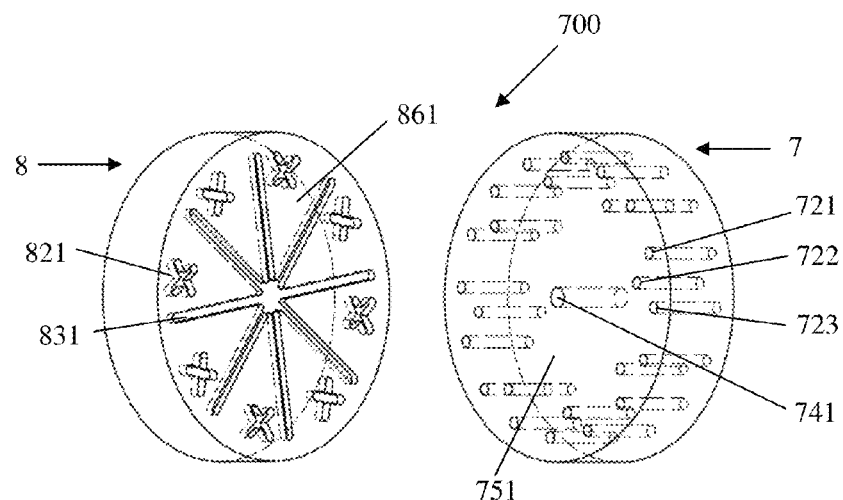
FIG. 17 is an exploded view of a fluid selection valve according to an example embodiment of the present invention.
Figures 18, 19:
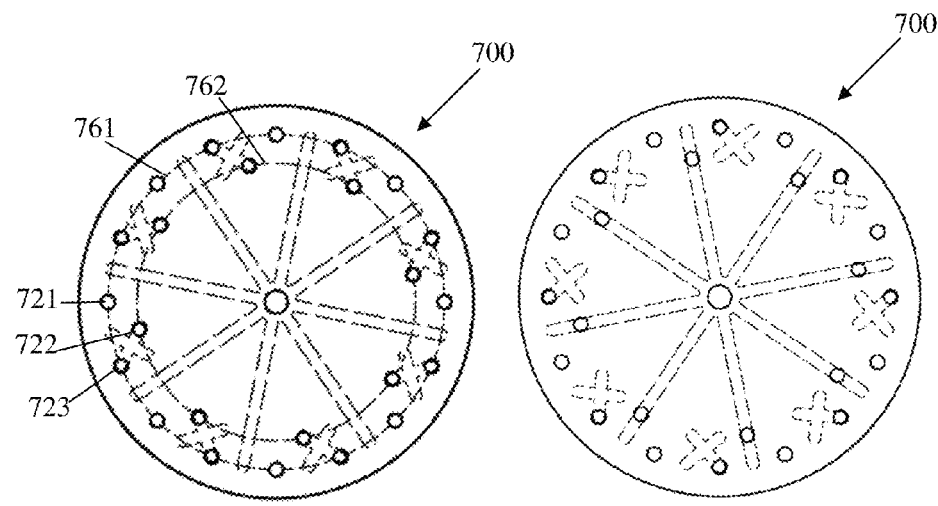
FIG. 18 is a top view of the fluid selection valve of FIG. 17 showing a port connection pattern.
FIG. 19 is a top view of the fluid selection valve of FIG. 17 showing another port connection pattern.

FIGS. 17 to 19 illustrate selection valve 700 according to an example embodiment. Selection valve 700 includes stator 7 and rotor 8. In this embodiment the ports around the central port 741 on the stator 7 are distributed on two imaginary circles. This embodiment is useful when more ports are needed. On stator 7 there are eight groups of ports. For each group the common port lies on imaginary circle 762 and their adjacent non-common ports lie on imaginary circle 761. For example, ports 721, 722, and 723 form one group with port 722 as the common port.

Rotor 8 has two types of channels on interface 861. The second channels comprise cross-shaped grooves, such as groove 821, which are used to provide fluid communication between the common ports and their adjacent non-common ports in their group. The first channels comprise grooves radiating from the center of rotor 8, such as groove 831, which are used to provide fluid communication between a central port 741 in the axial center of stator 7 and other ports around it. FIGS. 18 and 19 are top views of selection valve 700, with interface 861 of rotor 8 abutting interface 751 of stator 7. In FIG. 18 the common ports in each group is in fluid communication with one of their adjacent non-common ports in their group and central port 741 is blocked. In FIG. 19 central port 741 is in fluid communication with the eight common ports and the other non-common ports are blocked. By rotating rotor 8, the three connection statuses described in FIGS. 7 to 9 can also be achieved.

In alternative embodiments, first channels originating from central port 741, such as groove 831, may be disposed below the surface of interface 861 when it is desired to reduce contact of fluid with interface 751 of stator 7.

FIGS. 20 to 22 illustrate selection valve 900 according to an example embodiment. The difference between selection valve 900 and selection valve 700 is that in selection valve 900 the cross shaped grooves are replaced with trapezoidal grooves. This structure is more suitable when molding is used for the fabrication. Rotor 9 works with stator 7 in the same way as rotor 8.

FIGS. 21 and 22 are top views of selection valve 900, with interface 961 of rotor 9 abutting interface 751 of stator 7. In FIG. 21 the common ports (e.g., port 722) in each group are in fluid communication with adjacent first non-common ports (e.g., port 721) in their group and central port 741 is in fluid communication with second non-common ports (e.g. port 723). In FIG. 22 central port 741 is in fluid communication with the eight common ports and the other ports are blocked. By rotating rotor 9, the three connection statuses described in FIGS. 7 to 9 can also be achieved.

While a number of exemplary aspects and embodiments have been discussed above, those of skill in the art will recognize certain modifications, permutations, additions and sub-combinations thereof. The scope of the claims should not be limited by the preferred embodiments set forth in the examples, but should be given the broadest interpretation consistent with the description as a whole.

What is claimed is:

1. A fluid selection valve comprising:
   a stator comprising
      a stator interface;
      a plurality of ports arranged into a plurality of port groups, wherein each port group comprises at least three ports of which one is designated as a common port and the others are designated as non-common ports, the non-common ports comprising a first non-common port and a second non-common port, wherein each of the common ports, first non-common ports and the second non-common ports are circularly arranged at the stator interface;
   a rotor comprising
      a rotor interface abutting said stator interface;
      a plurality of first channels, each first channel extending from an axial center of the rotor to at least a point on the rotor interface alignable with the common ports for fluid communication therewith;
      a plurality of second channels, each second channel extending from at least a point on the rotor interface alignable with the common ports for fluid communication therewith to at least a point on the rotor interface alignable with the first non-common ports and/or the second non-common ports for fluid communication therewith;
   wherein at least one of the stator and the rotor comprises a central port located in an axial center thereof;
   wherein the rotor is coaxially rotatable relative to the stator to configure the fluid selection valve in at least three different positions;
   wherein in a first position, the common ports are in fluid communication with the central port via the first channels;
   wherein in a second position, the common ports are in fluid communication with the first non-common ports via the second channels; and
   wherein in a third position, the common ports are in fluid communication with the second non-common ports via the second channels.

2. A fluid selection valve according to claim 1, wherein an angular measure between a first channel and an adjacent first channel is equal to an angular measure between a common port in a port group and a common port in an adjacent port group.

3. A fluid selection valve according to claim 2, wherein the central port is located in the axial center of the stator.

4. A fluid selection valve according to claim 3, wherein the first channels and the second channels extend in a plane generally orthogonal to the axis of the rotor.

5. A fluid selection valve according to claim 4, wherein the rotor and the stator each comprise a substantially disc-shaped body.

6. A fluid selection valve according to claim 5, wherein the first channels comprise generally linear grooves on a surface of the rotor interface.

7. A fluid selection valve according to claim 5, wherein the first channels comprise bores within the rotor below a surface of the rotor interface.

8. A fluid selection valve according to claim 4, wherein the circular arrangements of the common ports, first non-common ports and the second non-common ports at the stator interface overlap.

9. A fluid selection valve according to claim 8, wherein the second channels comprise generally linear grooves on a surface of the rotor interface.

10. A fluid selection valve according to claim 9, wherein the plurality of ports comprise four port groups, and each port group comprises three ports of which one is designated as the common port and the other two are designated as the non-common ports, and wherein the rotor comprises four first channels and four second channels, wherein the length of each first channel is equal to a distance of the common port to the central port, and wherein the length of each second channel is equal to a distance of the common port to the non-common ports within the same port group.

11. A fluid selection valve according to claim 4, wherein the common ports are located on a first imaginary circle, the non-common ports are located on a second imaginary circle, and the first circle is concentric but non-overlapping with the second circle.

12. A fluid selection valve according to claim 11, wherein the second channels comprise a generally trapezoidal shape or a generally cross shape.

13. A fluid selection valve according to claim 2, wherein the central port is located in the axial center of the rotor.

14. A fluid selection valve according to claim 13, wherein the first channels extend in a plane generally orthogonal to the axis of the rotor and the second channels extend in a plane generally parallel to the axis of the rotor.

15. A fluid selection valve according to claim 14, wherein the stator comprises an annular or frustoconical annular body and the rotor comprises a cylindrical or frustoconical body configured for fitting engagement within the annular or frustoconical annular body of the stator.

\* \* \* \* \*

UNITED STATES PATENT AND TRADEMARK OFFICE
CERTIFICATE OF CORRECTION

| | | |
|---|---|---|
| PATENT NO. | : 8,813,785 B2 | |
| APPLICATION NO. | : 13/713996 | |
| DATED | : August 26, 2014 | |
| INVENTOR(S) | : Haibin Wan | |

It is certified that error appears in the above-identified patent and that said Letters Patent is hereby corrected as shown below:

On the Title page of the issued patent, the item (72) Inventor should be corrected as follows:

(72) Haibin Wan, Surrey (CA)

Signed and Sealed this
Thirtieth Day of December, 2014

Michelle K. Lee
*Deputy Director of the United States Patent and Trademark Office*